(12) United States Patent
Oppelt et al.

(10) Patent No.: US 6,212,131 B1
(45) Date of Patent: Apr. 3, 2001

(54) ULTRASOUND TRANSMITTING CIRCUIT AND ULTRASOUND TRANSMITTING SYSTEM HAVING A PLURALITY OF ULTRASOUND TRANSMITTING CIRCUITS

(75) Inventors: Ralph Oppelt, Uttenreuth; Wolfgang Renz, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/333,321

(22) Filed: Jun. 15, 1999

(30) Foreign Application Priority Data

Jun. 15, 1998 (DE) .............................................. 198 26 549

(51) Int. Cl.$^7$ ...................................................... H04B 1/02
(52) U.S. Cl. ...................................... 367/137; 310/316.01
(58) Field of Search ........................ 367/137; 310/316.01, 310/316.02; 327/4; 73/626

(56) References Cited

U.S. PATENT DOCUMENTS

| | | | |
|---|---|---|---|
| 4,275,363 | * 6/1981 | Mishiro et al. | 310/316.01 |
| 4,551,690 | * 11/1985 | Quist | 310/316.01 |
| 4,853,579 | * 8/1989 | Kawasaki et al. | 310/316.01 |
| 4,939,402 | * 7/1990 | Hirayama et al. | 310/316.01 |
| 4,970,656 | 11/1990 | Lo et al. . | |
| 5,001,442 | * 3/1991 | Hanaie et al. | 310/316.01 |
| 5,087,850 | * 2/1992 | Suzuta et al. | 310/316.01 |
| 5,216,338 | * 6/1993 | Wilson | 310/316.01 |

FOREIGN PATENT DOCUMENTS

4230491A1  3/1993 (DE) .

* cited by examiner

*Primary Examiner*—Ian J. Lobo
(74) *Attorney, Agent, or Firm*—Herbert L. Lerner; Laurence A. Greenberg; Werner H. Stemer

(57) ABSTRACT

An ultrasound transmitting circuit includes an electrical transmitter from which electrical oscillations can be fed at an electrical transmission power level over a connecting line into an ultrasound transducer. The electrical oscillations are formed of a current signal and a voltage signal. The ultrasound transducer can be excited by the electrical oscillations to produce ultrasound oscillations. In order to allow ultrasound oscillation power to be controlled more accurately, the current signal and the voltage signal can be supplied to a phase regulator. A variable impedance, which is coupled to the connecting line, can be actuated by the phase regulator in such a manner that the current signal and the voltage signal are in phase.

13 Claims, 1 Drawing Sheet

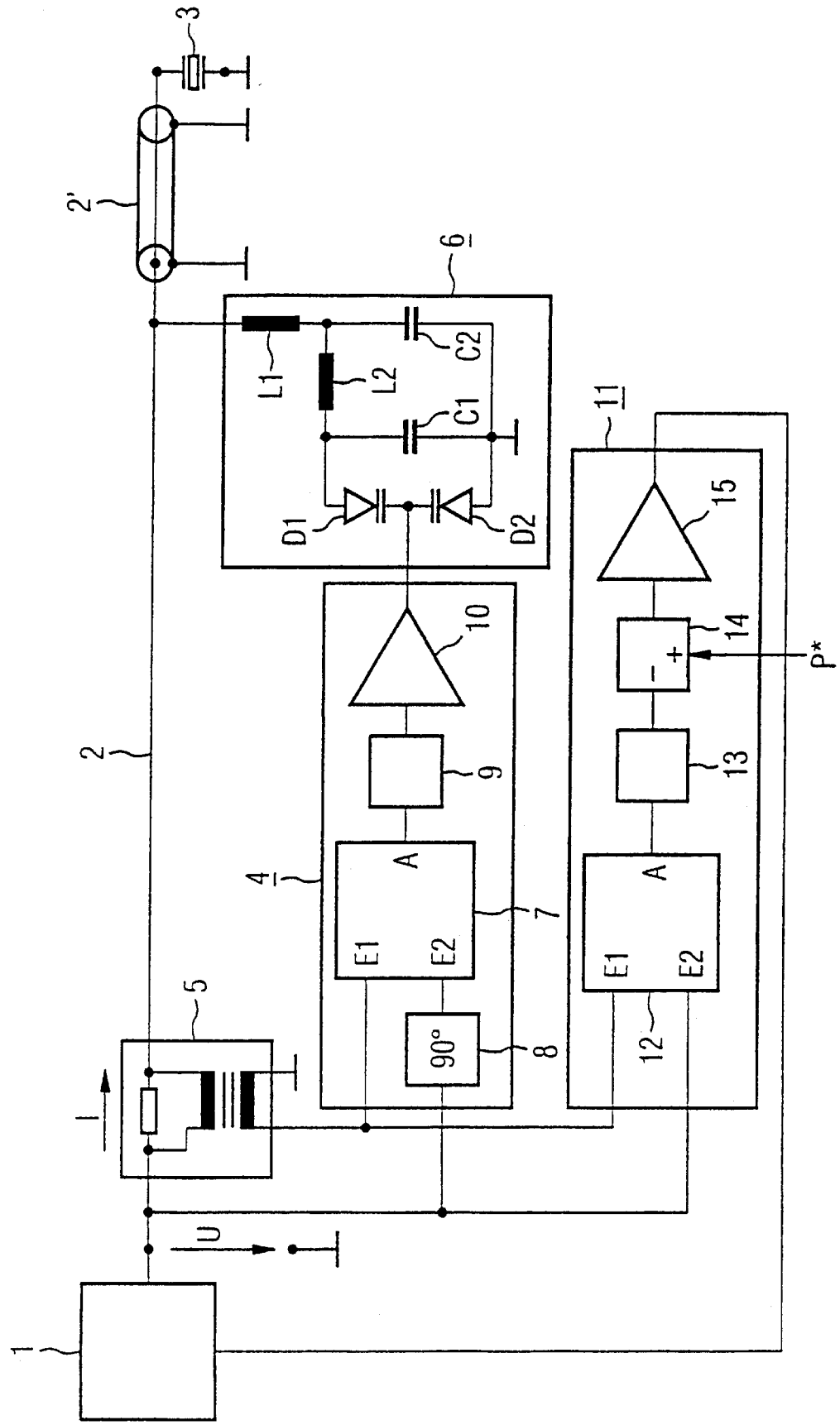

ULTRASOUND TRANSMITTING CIRCUIT AND ULTRASOUND TRANSMITTING SYSTEM HAVING A PLURALITY OF ULTRASOUND TRANSMITTING CIRCUITS

BACKGROUND OF THE INVENTION

Field of the Invention

The present invention relates to an ultrasound transmitting circuit including an electrical transmitter from which electrical oscillations, formed of a current signal and a voltage signal, can be fed at an electrical transmission power level over a connecting line into an ultrasound transducer that can be excited by the electrical oscillations to produce ultrasound oscillations.

Such an ultrasound transmitting circuit is used, for example, in therapeutic ultrasound arrays. The use of ultrasound arrays is dependent on a specific amplitude relationship, in addition to a specific phase relationship, between the individual ultrasound transducers in the ultrasound array. Major deviations from the predetermined relationship may cause serious deviations from the desired beam, which, under some circumstances, may even result in injuries to personnel.

The total power level fed in from the electrical transmitter can, in general, be preset very precisely. However, the individual ultrasound transducers have an impedance which, on one hand, is subject to major tolerances from one ultrasound transducer to another by virtue of the production techniques and, on the other hand, also varies dynamically as a function of the type of operation. Due to those impedance variations, the distribution of the transmitted ultrasound amplitudes deviates to a major extent from the predetermined electrical amplitude distribution of the individual electrical transmitters.

SUMMARY OF THE INVENTION

It is accordingly an object of the invention to provide an ultrasound transmitting circuit and an ultrasound transmitting system having a plurality of ultrasound transmitting circuits, which overcome the hereinafore-mentioned disadvantages of the heretofore-known devices of this general type and in which an amplitude of transmitted ultrasound oscillations can be predetermined exactly.

With the foregoing and other objects in view there is provided, in accordance with the invention, an ultrasound transmitting circuit, comprising an electrical transmitter for producing electrical oscillations formed of a current signal and a voltage signal; a connecting line connected to the electrical transmitter for carrying the electrical oscillations at an electrical transmission power level; an ultrasound transducer connected to the connecting line for receiving the electrical oscillations, the ultrasound transducer to be excited by the electrical oscillations to produce ultrasound oscillations; a phase regulator connected to the connecting line for receiving the current signal and the voltage signal; and a variable impedance connected to the phase regulator and coupled to the connecting line, the variable impedance to be actuated for placing the current signal and the voltage signal in phase.

When close to resonance, an ultrasound transducer behaves, to a first approximation, like a parallel circuit including a resistor and a capacitor. In accordance with another feature of the invention, the variable impedance is thus preferably configured as an inductance.

In accordance with a further feature of the invention, the relative phase of the current signal and the voltage signal can be controlled even more accurately if the inductance includes a fixed basic inductance and a variable, additional inductance, which can be actuated by the phase regulator.

In accordance with an added feature of the invention, the variable additional inductance can be achieved particularly easily if the additional inductance includes a quarter-wave circuit and at least one capacitance diode which is connected to the quarter-wave circuit and can be actuated by the phase regulator.

In accordance with an additional feature of the invention, a control signal for the variable inductance can be determined particularly easily if the phase regulator has a four-quadrant multiplier with two signal inputs and with one product output, a phase shifter is connected upstream of one of the signal inputs, the current signal and the voltage signal can be respectively supplied to one of the signal inputs, and the product output is connected to the variable impedance. The phase shifter allows the current signal and the voltage signal to be shifted through 90° with respect to one another, so that the electrical reactive power or volt-amperes can be measured through the use of the four-quadrant multiplier. Four-quadrant multipliers are available, for example, from the company Analog Devices, under the product designation MLT 04.

In accordance with yet another feature of the invention, there is provided a control amplifier connected downstream of the product output, in order to amplify the output signal from the four-quadrant multiplier.

In accordance with yet a further feature of the invention, the phase control is particularly stable if a low-pass filter is disposed between the product output and the control amplifier. The phase control results in the transmission power, which is fed in from the electrical transmitter, including only a real power component, but no reactive power or volt-amperes component. In principle, control of the transmitted power level is thus not absolutely essential.

In accordance with yet an added feature of the invention, the transmitted ultrasound oscillations can be controlled even more exactly if the current signal and the voltage signal can also be supplied to a power regulator, by which the electrical transmitter can be actuated in such a manner that the electrical transmission power level is regulated to a nominal power level.

In accordance with yet an additional feature of the invention, in the same way as the phase regulator, the power regulator may also have a four-quadrant multiplier with two signal inputs and one product output, the current signal and the voltage signal may be respectively supplied to one of the signal inputs, and the product output may be connected to the electrical transmitter.

In accordance with again another feature of the invention, once again, a low-pass filter is connected downstream of the product output.

In accordance with again a further feature of the invention, in order to allow the power level fed in from the electrical transmitter to be varied, a feed node, for presetting the nominal power level, is preferably connected upstream of the electrical transmitter.

In accordance with again an added feature of the invention, there is provided a control amplifier connected downstream of the feed node, in order to control the electrical transmitter power level even more precisely.

With the objects of the invention in view, there is also provided an ultrasound transmitting system, comprising a plurality of the ultrasound transmitting circuits coupled to one another.

Other features which are considered as characteristic for the invention are set forth in the appended claims.

Although the invention is illustrated and described herein as embodied in an ultrasound transmitting circuit and an ultrasound transmitting system having a plurality of ultrasound transmitting circuits, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWING

The FIGURE of the drawing is a schematic and diagrammatic view of an ultrasound transmitting circuit.

DESCRIPTION OF THE PREFERRED EMBODIMENTS

Referring now in detail to the single FIGURE of the drawing, there is seen an ultrasound transmitting circuit which has an electrical transmitter 1. The electrical transmitter 1 is connected through a connecting line 2 to an ultrasound transducer 3. According to the FIGURE, the connecting line 2 is configured as a coaxial line 2' in the vicinity of the ultrasound transducer 3.

Electrical oscillations at an electrical transmission power level P can be fed from the electrical transmitter 1 into the connecting line 2, and thus also to the ultrasound transducer 3. In this way, the ultrasound transducer 3 can be excited to produce ultrasound oscillations.

The electrical oscillations fed in from the electrical transmitter 1 include a current signal I and a voltage signal U. Thus, $$U(t)=U0 \cos \omega t \text{ and } I(t)=I0 \cos(\omega t+\phi)$$

where $U0$ is the maximum voltage, $I0$ is the maximum current, $\omega$ is the angular frequency, t is the time, and $\phi$ is the phase angle between the current signal I and the voltage signal U.

When close to resonance, the ultrasound transducer 3 behaves roughly like a resistor with a capacitance connected in parallel with it. In consequence, the current I leads the voltage U. The phase angle $\phi$ is thus between 0 and 90°, if no other measures are taken.

In order to ensure that the current signal I and the voltage signal U are in phase, that is to say the phase angle $\phi$ becomes 0, the current signal I and the voltage signal U can be supplied to a phase regulator 4. The current signal I in this case is converted into a corresponding voltage signal, through the use of an instrument transformer 5, before being supplied to the phase regulator 4. A variable impedance 6, which is coupled to the connecting line 2, can then be actuated by the phase regulator 4 in such a manner that the current signal I and the voltage signal U are in phase.

The variable impedance 6 includes a fixed basic inductance L1 and an adjustable, additional inductance, which can be actuated by the phase regulator 4. The additional inductance includes a quarter-wave circuit as well as two capacitance diodes D1, D2. The quarter-wave circuit is formed by two transformation capacitors C1, C2 and one transformation inductance L2. The capacitance diodes D1, D2 can be actuated by the phase regulator 4. The capacitance diodes D1, D2 act like an inductance, through the use of the quarter-wave circuit C1, C2, L2.

The phase regulator 4 has a four-quadrant multiplier 7 with two signal inputs E1, E2 and a product output A. A phase shifter 8 is connected upstream of the signal input E2. The phase shifter 8 in this case allows the voltage U to be shifted through (+ or −) 90°. Alternatively, it would also be possible to shift the current I through (+ or −) 90°.

The signal which is present at the product output A thus corresponds, on average, to the reactive volt-amperes or power fed into the connecting line 2 from the electrical transmitter 1. Thus, in order to smooth this signal, a low-pass filter 9 is connected downstream of the product output A and passes on the mean reactive power or voltage-amperes (including their mathematical sign) to a downstream control amplifier 10. The control amplifier 10 then actuates the capacitance diodes D1, D2 in such a manner that the average output signal which is present at the product output A turns to 0.

When the average signal which is present at the product output A is 0 the current signal I and the voltage signal U are in phase. Thus, only real power is fed into the connecting line 2. In order to regulate the transmission power level P, which includes only real power, at a nominal power level P*, the current signal I and the voltage signal U can also be supplied to a power regulator 11. The power regulator 11 can actuate the electrical transmitter 1 in such a manner that the electrical transmission power level P is regulated to the nominal power level P*.

The power regulator 11 also has a four-quadrant multiplier 12 with two signal inputs E1, E2 and a product output A. Once again, the current signal I and the voltage signal U can each be supplied to a respective one of the signal inputs E1, E2. However, in contrast to the phase regulator 4, the signals I, U can be supplied to this four-quadrant multiplier 11 without any phase shifter being connected therebetween. The mean output signal which is present at the product output A corresponds to the transmitted power level P. Thus, a low-pass filter 13 is once again connected downstream of the product output A, in order to smooth the output signal.

An output signal from the low-pass filter 13 is supplied to a feed node 14, in order to preset the nominal power level P*. A difference between the nominal power level P* and the transmitted power level P is formed in the feeder node 14. This difference is supplied to a control amplifier 15, having an output signal which is then supplied to the electrical transmitter 1, so that the transmission power level P can be corrected.

The ultrasound transmitting circuit described above can, in principle, be operated in isolation from other ultrasound transmitting circuits. However, its use is particularly advantageous in an ultrasound transmitting system which has a plurality of mutually coupled ultrasound transmitting circuits, with each of the ultrasound transmitting circuits being configured as described above.

We claim:

1. An ultrasound transmitting circuit, comprising:
   an electrical transmitter for producing electrical oscillations formed of a current signal and a voltage signal;
   a connecting line connected to said electrical transmitter for carrying the electrical oscillations at an electrical transmission power level;
   an ultrasound transducer connected to said connecting line for receiving the electrical oscillations, said ultrasound transducer to be excited by the electrical oscillations to produce ultrasound oscillations;

a phase regulator connected to said connecting line for receiving the current signal and the voltage signal; and a variable impedance connected to said phase regulator and coupled to said connecting line, said variable impedance to be actuated for placing the current signal and the voltage signal in phase.

2. The ultrasound transmitting circuit according to claim 1, wherein said variable impedance is an inductance.

3. The ultrasound transmitting circuit according to claim 2, wherein said inductance includes a fixed basic inductance and a variable, additional inductance to be actuated by said phase regulator.

4. The ultrasound transmitting circuit according to claim 3, wherein said additional inductance includes a quarter-wave circuit and at least one capacitance diode connected to said quarter-wave circuit and to be actuated by said phase regulator.

5. The ultrasound transmitting circuit according to claim 1, wherein said phase regulator includes:

a four-quadrant multiplier having two signal inputs and a product output, said signal inputs each receiving a respective one of the current and voltage signals, and said product output connected to said variable impedance; and a phase shifter connected upstream of one of said signal inputs.

6. The ultrasound transmitting circuit according to claim 5, including a control amplifier connected downstream of said product output.

7. The ultrasound transmitting circuit according to claim 6, including a low-pass filter connected between said product output and said control amplifier.

8. The ultrasound transmitting circuit according to claim 1, including a power regulator connected to said connecting line and to said electrical transmitter, for receiving the current signal and the voltage signal and for actuating said electrical transmitter for regulating the electrical transmission power level to a nominal power level.

9. The ultrasound transmitting circuit according to claim 8, wherein said power regulator includes a four-quadrant multiplier having two signal inputs and a product output, said signal inputs each receive a respective one of the current and voltage signals, and said product output is connected to said electrical transmitter.

10. The ultrasound transmitting circuit according to claim 9, including a low-pass filter connected downstream of said product output.

11. The ultrasound transmitting circuit according to claim 8, wherein said power regulator includes a feed node connected upstream of said electrical transmitter, for presetting the nominal power level.

12. The ultrasound transmitting circuit according to claim 11, wherein said power regulator includes a control amplifier connected downstream of said feed node.

13. An ultrasound transmitting system, comprising:

a plurality of ultrasound transmitting circuits coupled to one another, each of said ultrasound transmitting circuits including:

an electrical transmitter for producing electrical oscillations formed of a current signal and a voltage signal;

a connecting line connected to said electrical transmitter for carrying the electrical oscillations at an electrical transmission power level;

an ultrasound transducer connected to said connecting line for receiving the electrical oscillations, said ultrasound transducer to be excited by the electrical oscillations to produce ultrasound oscillations;

a phase regulator connected to said connecting line for receiving the current signal and the voltage signal; and a variable impedance connected to said phase regulator and coupled to said connecting line, said variable impedance to be actuated for placing the current signal and the voltage signal in phase.

* * * * *